United States Patent
Peters et al.

(10) Patent No.: US 10,285,715 B2
(45) Date of Patent: May 14, 2019

(54) SURGICAL INSTRUMENT AND METHOD

(71) Applicant: Warsaw Orthopedic, Inc., Warsaw, IN (US)

(72) Inventors: Jesse W. Peters, Memphis, TN (US); Jerald L. Redmond, Germantown, TN (US); Nicholas M. Benson, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 594 days.

(21) Appl. No.: 14/977,161

(22) Filed: Dec. 21, 2015

(65) Prior Publication Data

US 2017/0172589 A1 Jun. 22, 2017

(51) Int. Cl.
| | | |
|---|---|---|
| *A61B 17/16* | (2006.01) | |
| *A61B 17/17* | (2006.01) | |
| *A61B 17/90* | (2006.01) | |
| *A61B 90/50* | (2016.01) | |
| *A61B 90/00* | (2016.01) | |
| *A61B 34/20* | (2016.01) | |

(52) U.S. Cl.
CPC ...... *A61B 17/1757* (2013.01); *A61B 17/1655* (2013.01); *A61B 17/1703* (2013.01); *A61B 90/50* (2016.02); *A61B 2017/90* (2013.01); *A61B 2034/2051* (2016.02); *A61B 2034/2055* (2016.02); *A61B 2090/3764* (2016.02); *A61B 2090/3966* (2016.02); *A61B 2090/504* (2016.02)

(58) Field of Classification Search
CPC ........ A61B 2090/504; A61B 2217/002; A61B 5/02438; A61B 17/1617; A61B 2034/2055

See application file for complete search history.

(56) References Cited

U.S. PATENT DOCUMENTS

| | | | | |
|---|---|---|---|---|
| 3,871,236 | A * | 3/1975 | De la Cierva | F41G 5/16 74/5.22 |
| 6,122,538 | A * | 9/2000 | Sliwa, Jr. | A61B 8/00 324/207.14 |
| 7,404,268 | B1 * | 7/2008 | Page | F41G 1/38 42/126 |
| 2003/0076421 | A1 * | 4/2003 | Dutta | H04N 5/23248 348/208.11 |
| 2003/0089389 | A1 * | 5/2003 | Meador | A45B 3/00 135/65 |
| 2007/0238999 | A1 * | 10/2007 | Specht | A61B 5/02007 600/437 |
| 2008/0319313 | A1 * | 12/2008 | Boivin | A61B 34/20 600/424 |
| 2010/0026550 | A1 * | 2/2010 | Rosenbury | A61B 5/02438 342/22 |
| 2010/0079101 | A1 * | 4/2010 | Sidman | F16M 11/041 318/649 |
| 2010/0324437 | A1 * | 12/2010 | Freeman | A61B 5/085 600/529 |
| 2011/0211164 | A1 * | 9/2011 | Monroe | F16M 11/14 352/243 |

(Continued)

*Primary Examiner* — David W Bates

(57) ABSTRACT

A surgical instrument comprises a member configured for connection to an image guide defining an axis and being oriented relative to a sensor to communicate a signal representative of a position of the member. A stabilizer is aligned with the axis and configured to resist and/or prevent movement of the image guide from the orientation. Systems and methods are disclosed.

20 Claims, 8 Drawing Sheets

(56) References Cited

U.S. PATENT DOCUMENTS

| | | | |
|---|---|---|---|
| 2011/0245659 A1* | 10/2011 | Ma | A61B 5/066 600/424 |
| 2012/0143084 A1* | 6/2012 | Shoham | A61B 17/1675 600/567 |
| 2012/0194486 A1* | 8/2012 | Kajitani | G06F 3/03545 345/179 |
| 2012/0270186 A1* | 10/2012 | Singh | F41A 33/00 434/19 |
| 2013/0064427 A1* | 3/2013 | Picard | G01S 5/163 382/103 |
| 2016/0113720 A1* | 4/2016 | Lavallee | A61B 17/15 606/130 |
| 2016/0157815 A1* | 6/2016 | Slak | A61B 8/0841 433/29 |
| 2016/0361070 A1* | 12/2016 | Ardel | A61B 17/1626 |
| 2016/0377372 A1* | 12/2016 | Hodgson | F41A 21/30 42/1.06 |
| 2017/0027416 A1* | 2/2017 | Hayashi | A61B 1/00009 |
| 2017/0348037 A1* | 12/2017 | Sexson | A61B 34/30 |

\* cited by examiner

1

SURGICAL INSTRUMENT AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. For example, fusion and fixation treatments may be performed that employ implants to restore the mechanical support function of vertebrae. Surgical instruments are employed, for example, to prepare tissue surfaces for disposal of the implants. Surgical instruments are also employed to engage implants for disposal with the tissue surfaces at a surgical site. This disclosure describes an improvement over these prior technologies.

SUMMARY

In one embodiment, a surgical instrument is provided. The surgical instrument comprises a member configured for connection to an image guide defining an axis and being oriented relative to a sensor to communicate a signal representative of a position of the member. A stabilizer is aligned with the axis and configured to resist and/or prevent movement of the image guide from the orientation. In some embodiments, surgical systems and methods are provided.

BRIEF DESCRIPTION OF THE DRAWINGS

The present disclosure will become more readily apparent from the specific description accompanied by the following drawings, in which.

DETAILED DESCRIPTION

Figure 1:
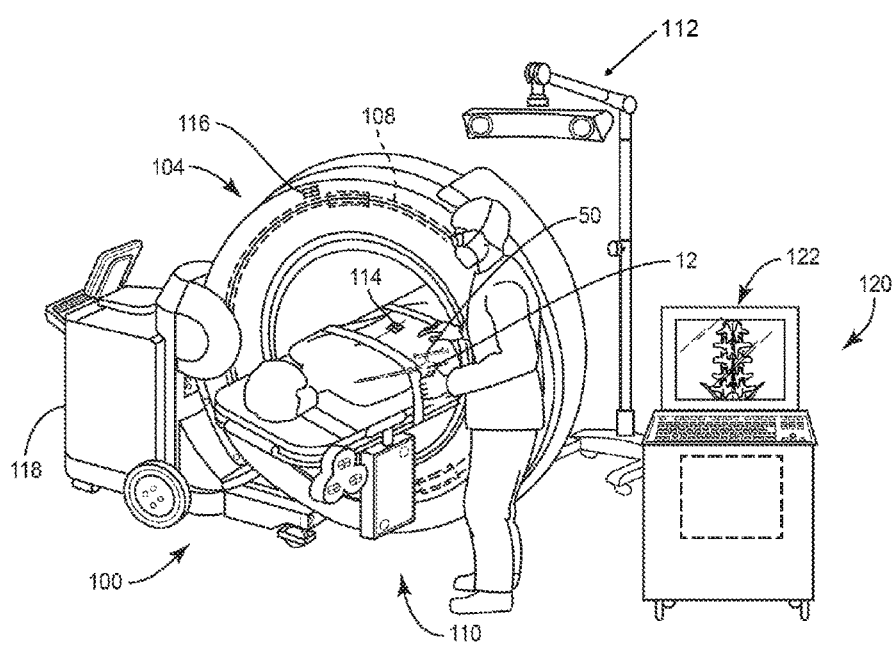
FIG. 1 is a plan view of one embodiment of a surgical system in accordance with the principles of the present disclosure.
Figure 2:
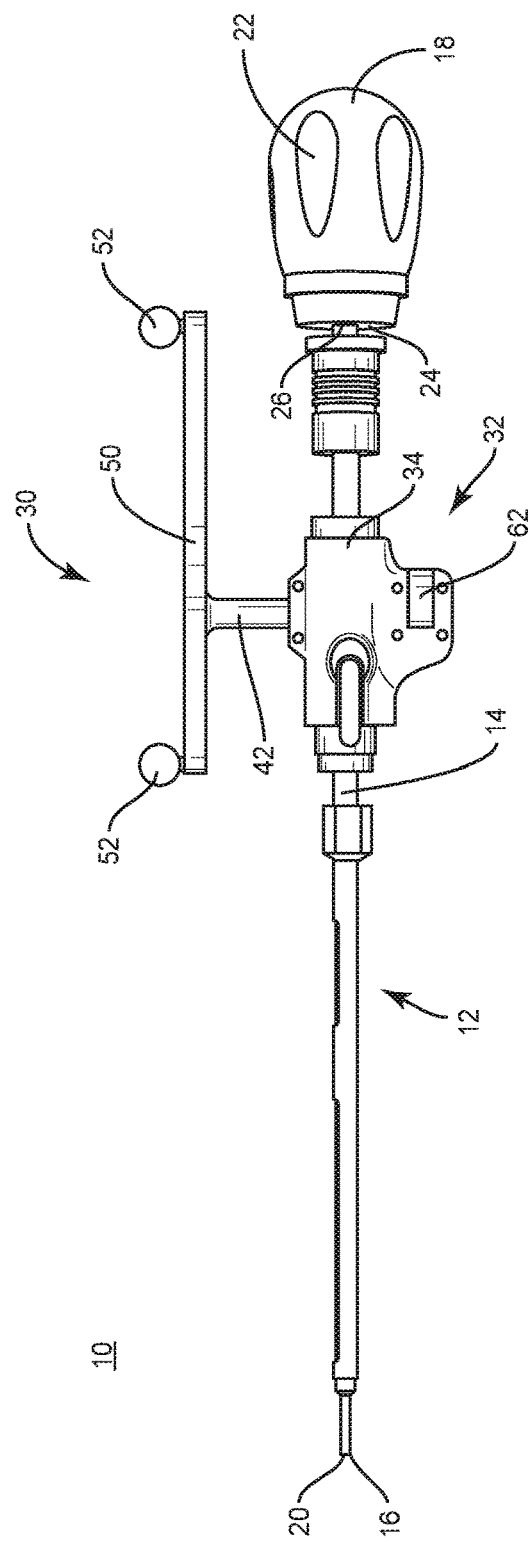
FIG. 2 is a perspective view of components of one embodiment of a surgical system in accordance with the principles of the present disclosure.
Figure 3:
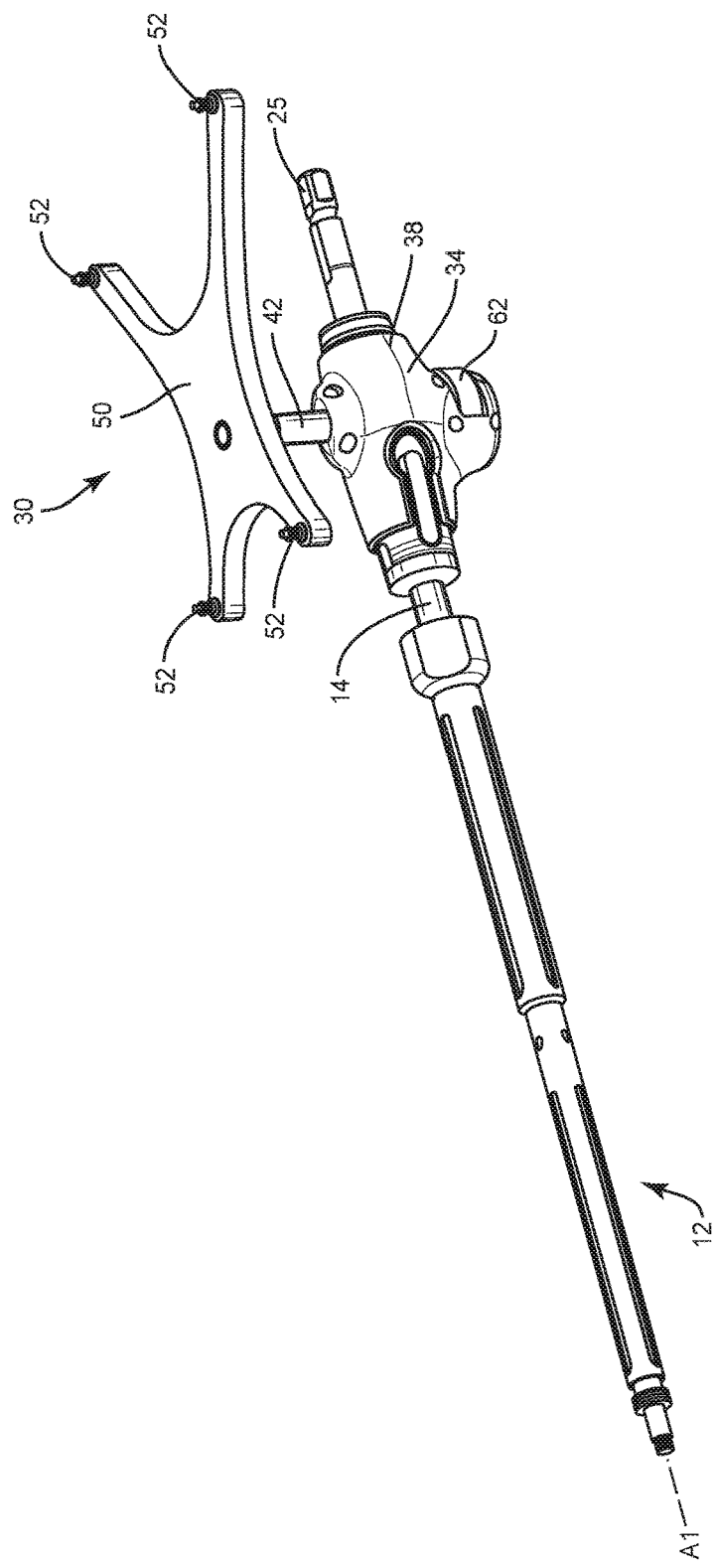
FIG. 3 is a perspective view of components of one embodiment of a surgical system in accordance with the principles of the present disclosure.
Figure 4:
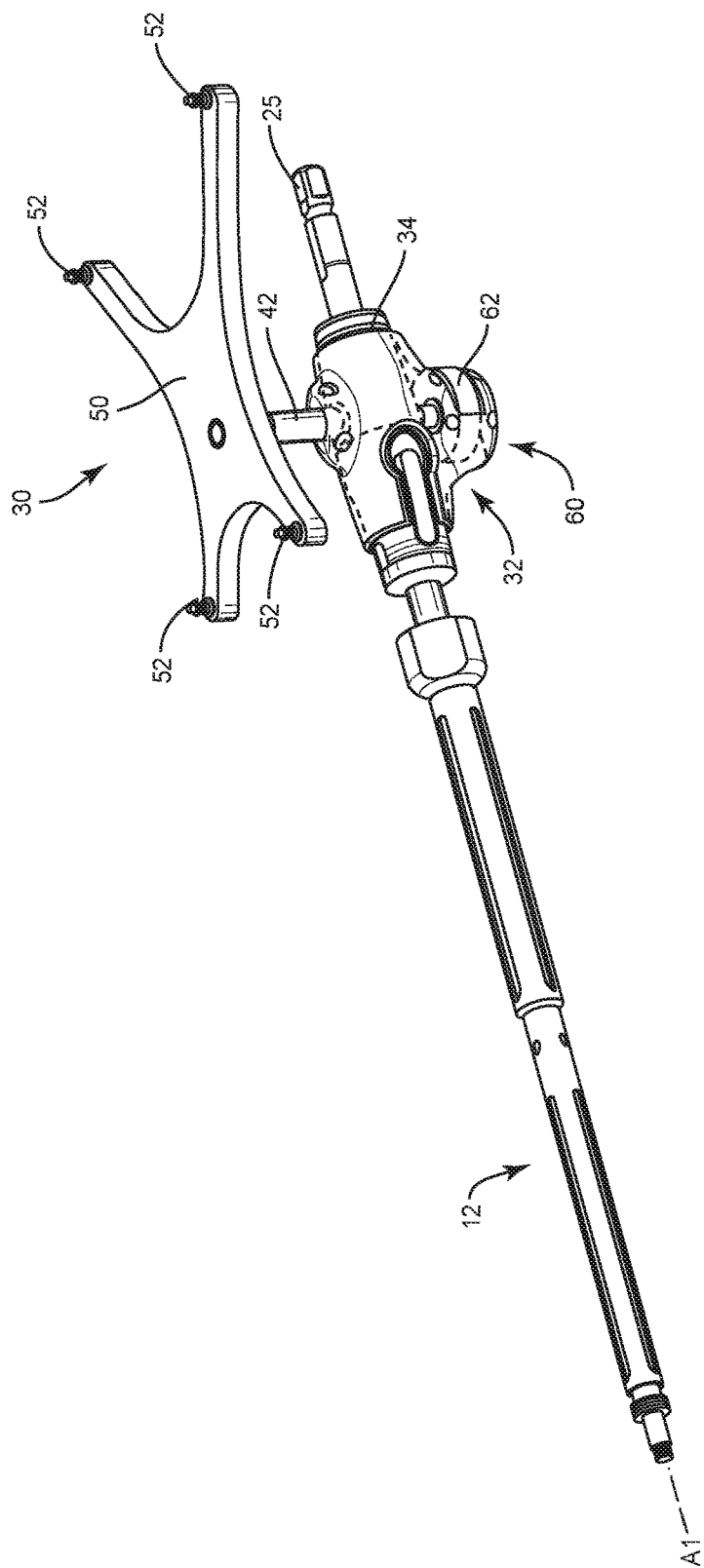
FIG. 4 is a perspective view, in part phantom, of the components shown in FIG. 3.

The exemplary embodiments of a surgical system are discussed in terms of medical devices for the treatment of musculoskeletal disorders and more particularly, in terms of a surgical system and a method for treating a spine. In some embodiments, the surgical system includes a surgical instrument having an image guide, such as, for example, a surgical navigation tracker and a stabilizer for maintaining tracker orientation.

In some embodiments, the surgical system includes a surgical instrument including gyroscopic stabilization for maintaining navigated instrument tracker orientation. In some embodiments, the surgical system includes a surgical instrument having a surgical navigation tracker and a gyroscopic stabilizer for maintaining tracker orientation with a sensor. In some embodiments, the surgical instrument includes a surgically navigated instrument, such as, for example, a drill, driver, or tap, which freely rotates about a centerline axis. In some embodiments, the surgical instrument includes a navigation tracker that is optically tracked and requires a line-of-sight view to a sensor, such as, for example, a camera.

In some embodiments, the surgical instrument includes gyroscopic stabilization comprising a gyroscope. In some embodiments, the gyroscope includes a spinning wheel that defines a spin axis and the surgical instrument aligns the navigation tracker with the spin axis. In some embodiments, the gyroscope maintains the navigation tracker orientation with the spin axis based on conservation of angular momentum to resist and/or prevent movement of the navigation tracker out of alignment with the sensor. In some embodiments, the gyroscope maintains the tracker orientation such that the surgical instrument is not affected by tilting or rotational effects on the surgical instrument. In some embodiments, the navigation tracker is connected with a post to the surgical instrument and the post is aligned with the spin axis. In some embodiments, the gyroscope maintains tracker orientation by aligning the spin axis with the post, and maintains tracker orientation independent of surgical instrument movement. In some embodiments, the gyroscope may be powered electronically, such as, for example, via a battery, AC current and/or DC current. In some embodiments, the gyroscope may be powered pneumatically, such as, for example, a compressed air cartridge.

In some embodiments, the surgical system includes a navigation tracker attached to a surgical instrument and is disposed in a direct line of sight of a sensor, which includes one or more cameras. In some embodiments, the surgical system includes a medical imaging device that digitally captures images of an anatomy. In some embodiments, the tracker communicates with a surgical navigation system to determine and/or display surgical instrument positioning relative to the anatomy. In some embodiments, the surgical instrument includes gyroscopic stabilization and employs its angular momentum to overcome forces exerted on surgical instrument, for example, by a surgeon or a patient.

In some embodiments, the surgical instrument includes gyroscopic stabilization comprising a housing mounted to the surgical instrument that supports a gyroscope. In some embodiments, the gyroscope is disposed adjacent a bottom surface of the housing and/or surgical instrument. In some embodiments, the gyroscope is disposed adjacent an upper surface of the housing and/or surgical instrument. In some embodiments, the surgical instrument includes one or more stabilizers. In some embodiments, the surgical instrument includes a stabilizer that includes a counterbalance, for example, via a selectively positioned weight. In some embodiments, the surgical instrument includes a stabilizer that provides a counterbalance effect and gyroscopic stabilization.

In some embodiments, one or all of the components of the surgical system may be disposable, peel pack and/or pre packed sterile devices. One or all of the components of the surgical system may be reusable. The surgical system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with an open or mini-open, minimal access and/or minimally invasive including percutaneous surgical technique to prepare tissue surfaces and/or engage implants, as described herein. In some embodiments, surgical system 10 is employed to create a cavity within a body of a patient, for example, a section of a spine for an implant, such as, for example, a bone fastener at a surgical site.

Surgical system 10 comprises a surgical instrument 12 that includes a member, such as, for example, a shaft 14. Shaft 14 extends between an end 16 and an end 18. Shaft 14 defines a longitudinal axis A1. In some embodiments, all or a portion of shaft 14 may have alternate cross section configurations, such as, for example, circular, oval, oblong, triangular, square, hexagonal, polygonal, irregular, uniform, non-uniform and/or tapered. In some embodiments, surgical instrument 12 may include a member that comprises and/or is connected with a tap, drill or a screwdriver.

End 16 includes an engagement surface, such as, for example, an implant engaging surface 20. In some embodiments, implant engaging surface 20 comprises a driver and is configured for engagement with a spinal implant, such as, for example, a bone fastener. In some embodiments, implant engaging surface 20 may include a square, triangular, hexagonal, polygonal, star, torx or hexalobe cross section configured to engage a correspondingly shaped portion of a spinal implant. In some embodiments, implant engaging surface 20 may have alternate cross section configurations, such as, for example, oval, oblong, irregular, uniform, non-uniform and/or tapered. In some embodiments, end 16 includes an engagement surface that comprises a tissue engagement surface and/or a tissue preparation surface, such as, as a drill, tap or awl for penetrating and/or creating a cavity in tissue. In some embodiments, end 16 includes an engagement surface that comprises a sleeve, cannula or trocar for engaging tissue and/or an implant.

End 18 includes a handle 22 configured to facilitate manipulation of surgical instrument 12. Handle 22 includes a mating surface 24 that defines a cavity 26 configured for disposal of an instrument and/or a tool extension, such as, for example, a mating surface 25 of shaft 14, as discussed herein. Cavity 26 is centrally positioned with respect to handle 22. In some embodiments, mating surface 25 may include a square, triangular, hexagonal, polygonal, star, torx or hexalobe cross section configured engage a correspondingly shaped portion of mating surface 24. In some embodiments, cavity 26 may have various cross-section configurations, such as, for example, oval, oblong, triangular, rectangular, square, polygonal, irregular, uniform, non-uniform, variable, tubular and/or tapered. In some embodiments, mating surface 24 may have various surface configurations to facilitate engagement with mating surface 25, such as, for example, rough, arcuate, undulating, porous, semi-porous, dimpled, polished and/or textured.

In some embodiments, mating surface 25 defines a connection portion configured for releasable engagement with an actuator, such as, for example, a powered drill, hand drill or other tool (not shown). In some embodiments, handle 22 may have alternate cross section configurations, such as, for example, oval, oblong, triangular, square, hexagonal, polygonal, irregular, uniform, non-uniform and/or tapered. In some embodiments, handle 22 may be disposed at alternate orientations relative to end 18 and/or end 16, such as, for example, transverse, perpendicular and/or other angular orientations such as acute or obtuse.

Shaft 14 is configured for connection with an image guide, such as, for example, a navigation component 30, as described herein. Navigation component 30 is configured to generate a signal representative of a position of surgical instrument 12. In some embodiments, the image guide may include one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

Navigation component 30 includes a housing 32 configured for disposal with shaft 14. Housing 32 is rotatable relative to shaft 14 about axis A1. In some embodiments, housing 32 is axially fixed with shaft 14 such that housing 32 is connected with shaft 14 and axial translation of housing 32 relative to shaft 14 is resisted and/or prevented. Housing 32 includes a collar 34 having a surface 36 that defines a passageway 38.

Passageway 38 is configured for disposal of shaft 14 and to receive shaft 14 to connect navigation component 30 with surgical instrument 12. Surface 36 slidably engages an outer surface of shaft 14 to facilitate rotation of housing 32 relative to shaft 14. In some embodiments, collar 34 is configured for connection with a flange disposed with shaft 14. In some embodiments, housing 32 is connected with shaft 14 via friction fit, pressure fit, interlocking engagement, mating engagement, dovetail connection, hook and loop closure, clips, barbs, tongue in groove, threaded, magnetic, key/keyslot, drill chuck and/or adhesive.

Housing 32 includes a post 42 extending from collar 34. Post 42 defines an axis X1. Post 42 extends perpendicular to axis A1 and is rotatable with housing 32 relative to shaft 14 about axis A1. In some embodiments, post 42 is axially fixed with shaft 14 such that axial translation of post 42 relative to shaft 14 is resisted and/or prevented. In some embodiments, post 42 may be adjusted in an axial direction relative to shaft 14. In some embodiments, axis X1 may be disposed at alternate orientations relative to axis A1, such as, for example, parallel, transverse and/or other angular orientations, such as, acute or obtuse.

Navigation component 30 includes a tracking device having an emitter array 50 that extends from and is connected to housing 32 via post 42. Emitter array 50 is rotatable with housing 32 relative to shaft 14 about axis A1. In some embodiments, emitter array 50 is axially fixed with shaft 14 such that axial translation of emitter array 50 relative to shaft 14 is resisted and/or prevented. In some embodiments, emitter array 50 may be adjusted in rotation and/or an axial direction relative to post 42 and/or shaft 14. In some embodiments, emitter array 50 may be disposed at alternate orientations relative to axis A1, such as, for example, parallel, perpendicular, transverse and/or other angular orientations, such as, acute or obtuse.

Emitter array 50 is configured for generating a signal representing a spatial position and/or a trajectory of surgical instrument 12 relative to a portion of a patient's anatomy and/or a depth of a spinal implant within the patient's anatomy. Emitter array 50 includes four spaced apart arms having a substantially X-shape. Emitter array 50 includes markers, such as, for example fiducials 52. Fiducials 52 appear in an image produced by a surgical navigation system 100, as shown in FIG. 1, for use as a point of reference or a measure. Emitter array 50 generates signals representing the position of various body reference points of the patient's anatomy.

Surgical instrument 12 is configured for disposal adjacent a surgical site such that navigation component 30 is oriented relative to a sensor array 112 of a surgical navigation system 100 of surgical system 10, as shown in FIG. 1. Orientation of navigation component 30 relative to sensor array 112 facilitates communication between navigation component 30 and sensor array 112 during a surgical procedure, as described herein. Sensor array 112 receives signals from emitter array 50 to provide information regarding the spatial position and/or trajectory of surgical instrument 12 relative to a portion of the patient's anatomy, as described herein. See, for example, similar surgical navigation components and their use as described in U.S. Pat. Nos. 6,021,343, 6,725,080, 6,796,988, the entire contents of each of these references being incorporated by reference herein. In some embodiments, navigation component 30 includes at least one light emitting diode. In some embodiments, navigation component 30 may include other tracking devices capable of being tracked by sensor array 112, such as, for example, a tracking device that actively generates acoustic signals, magnetic signals, electromagnetic signals, radiologic signals.

Housing 32 includes a surface 44 that defines a cavity 46. Cavity 46 is configured for disposal of a stabilizer, such as, for example, a gyroscope 60. Cavity 46 and gyroscope 60 disposed therein are positioned such that shaft 14 and housing 32 are disposed between emitter array 50 and the assembly of gyroscope 60 with cavity 46. As such, emitter array 50 and cavity 46/gyroscope 60 are disposed on opposing sides of shaft 14 and housing 32.

Gyroscope 60 includes a member, such as, for example, a rod 64. Surface 44 defines channels 65 configured for disposal of rod 64 to connect gyroscope 60 with housing 32. Rod 64 rotates within channels 65 to facilitate rotation of gyroscope 60 relative to housing 32. In some embodiments, the stabilizer is rotatable relative to shaft 14 about axis A1. In some embodiments, the stabilizer is axially fixed with shaft 14 such that axial translation of the stabilizer relative to shaft 14 is resisted and/or prevented. In some embodiments, the stabilizer may be adjusted in rotation and/or an axial direction relative to shaft 14. In some embodiments, the stabilizer includes a counter-balance weight or mass disposed with cavity 46.

In some embodiments, gyroscope 60 includes a wheel 62 that is manipulated and/or powered, as described herein, to rotate relative to housing 32. Wheel 62 defines a spin axis X2 about which wheel 62 rotates. Axis X2 is disposed perpendicular to axis A1. In some embodiments, axis X2 may be disposed at alternate orientations relative to axis A1, such as, for example, parallel, transverse and/or other angular orientations, such as, acute or obtuse.

Figure 5:
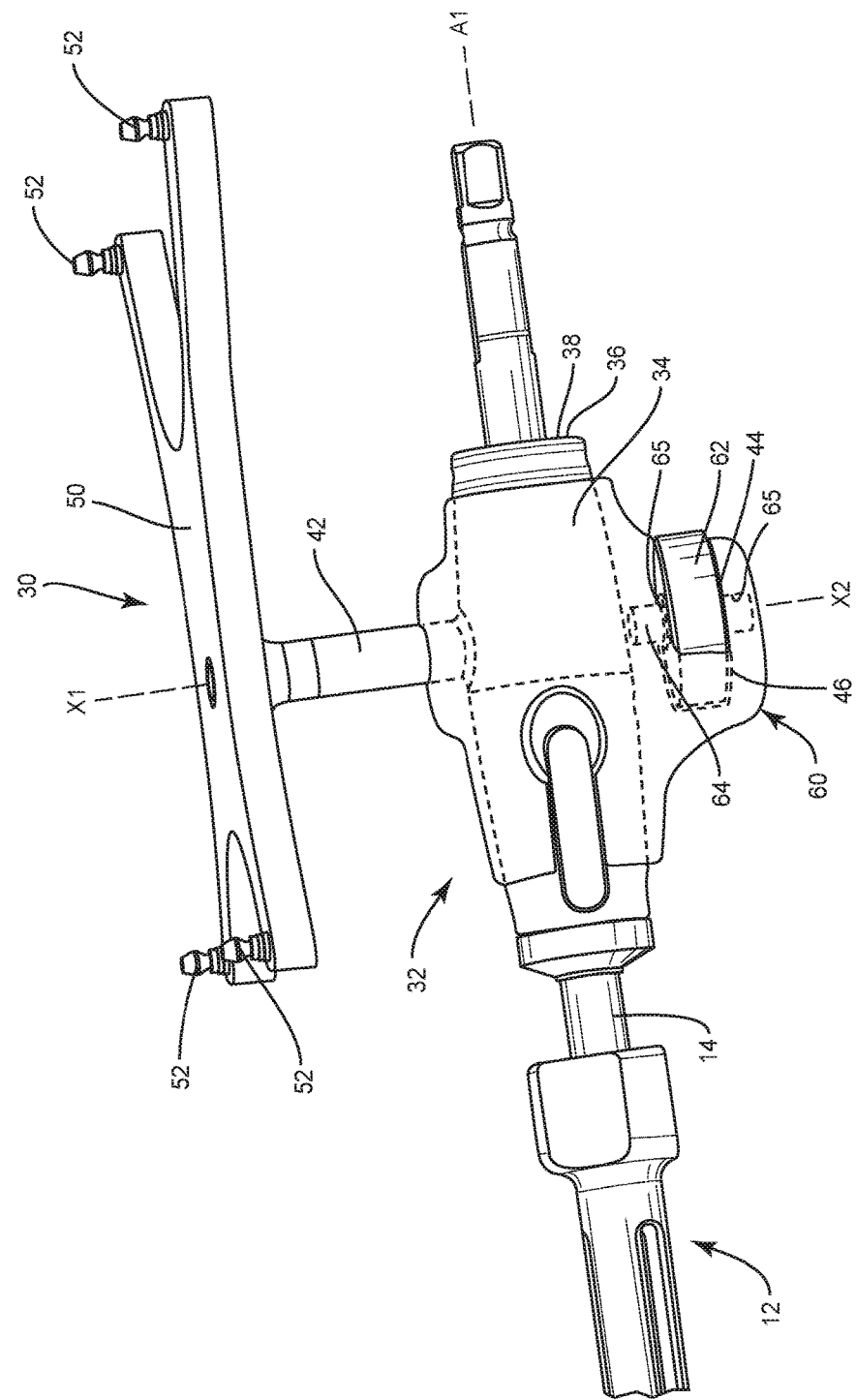
FIG. 5 is a break away view of components shown in FIG. 4.

Spin axis X2 is aligned with axis X1 such that spin axis X2 is co-axial with axis X1, as shown in FIG. 5. Gyroscope 60 maintains an alignment and/or orientation of navigation emitter array 50 relative to sensor array 112 to communicate a signal representative of a position of surgical instrument 12 and/or an implant connected thereto, as housing 32 is urged and/or moved to rotate and/or translate about and/or relative to axis A1 of shaft 14 during manipulation of surgical instrument 12 in a surgical procedure. Wheel 62 is configured to rotate about axis X2 to maintain the alignment and/or orientation of emitter array 50 for communicating the signal relative to sensor array 112. Rotation of wheel 62 is configured to resist and/or prevent movement of navigation component 30 from the alignment and/or orientation for communicating the signal representative of the position of surgical instrument 12 relative to sensor array 112.

Wheel 62 is manipulated and/or powered, as described herein, to rotate relative to housing 32 and generate an angular momentum. In some embodiments, the generation of the angular momentum of wheel 62 is determined based on a speed of rotation of wheel 62, a mass of wheel 62, and distribution of the mass. Wheel 62 is configured to conserve angular momentum such that variation in the alignment and/or orientation of navigation component 30, such as, for example, tilting, translating and/or rotating of surgical instrument 12 and/or navigation component 30 is reacted to and compensated for by gyroscope 60 by an equal and opposite force. In some embodiments, gyroscope 60 reacts to such variations so that the net force effect is zero to resist and/or prevent movement of navigation component 30 from the alignment and/or orientation for communicating the signal representative of the position of surgical instrument 12 relative to sensor array 112.

In some embodiments, rod 64 and/or wheel 62 are connected to a power source to rotate wheel 62, as described herein, about axis X2. For example, rod 64 and/or wheel 62 can be connected to an actuator, such as, for example, an electric motor that rotates wheel 62, which is connected to an electrical power source that powers the electric motor. In some embodiments, the power source includes an electrical power source, such as, for example, a cord connection to an electrical outlet. In some embodiments, the power source includes a battery. In some embodiments, the battery is powered from an external device via telemetry (near-field communication, for example). In some embodiments, the power source includes a pneumatic power source, such as, for example, a compressed air device that delivers air to an actuator, which includes blades and/or vanes connected with rod 64 and/or wheel 62 such that wheel 62 is rotated. In some embodiments, the power source includes a compressed air cartridge. In some embodiments, the power source is a hydraulic power source that delivers fluid to blades and/or vanes connected with rod 64 and/or wheel 62 such that wheel 62 is rotated.

In some embodiments, an actuator that is connected with rod 64 and/or wheel 62 for rotating wheel 62, as described herein, and a power source, can be disposed internal with housing 32, external and attached to housing 32 and/or external and separate to housing 32, for example, remote. In some embodiments, the actuator includes a mechanical rotating or spinning device that is positioned remotely, for example on a surgical table, from surgical instrument 12. Surgical instrument 12 is disposed adjacent to the spinning device and the spinning device is engaged with wheel 62 to rotate or spin wheel 62, as described herein, for a period of time. Upon depletion of the rotational energy imparted to wheel 62, surgical instrument 12 can again be disposed adjacent to the spinning device and the spinning device is engaged with wheel 62 to rotate or spin wheel 62. In some embodiments, surgical instrument 12 is positionable within, external and attached, external and separate, adjacent and/or formed with an actuator that includes a mechanical rotating or spinning device for rotating wheel 62, as described herein. In some embodiments, the mechanical rotating or spinning device is configured to impart rotation or spin to wheel 62, which may or may not include rotation of the spinning device. In some embodiments, the mechanical rotating or spinning device is actuated for continuous rotation during a surgical procedure, as described herein, to impart rotation or spin to wheel 62. In some embodiments, the mechanical rotating or spinning device is actuated for intermittent and/or sequential rotation during a surgical procedure, as described herein, to impart rotation or spin to wheel 62. In some embodiments, the mechanical rotating or spinning device is selectively actuated, for example powering on and off, for rotation during a surgical procedure, as described herein, to impart rotation or spin to wheel 62.

Surgical navigation system 100 is configured for acquiring and displaying medical imaging, such as, for example, x-ray images appropriate for a given surgical procedure, as shown in FIG. 1. In some embodiments, pre-acquired images of a patient are collected. In some embodiments, surgical navigation system 100 can include an O-arm® imaging device 104 sold by Medtronic Navigation, Inc. having a place of business in Louisville, Colo., USA. Imaging device 104 may have a generally annular gantry housing that encloses an image capturing portion 108.

In some embodiments, image capturing portion 108 may include an x-ray source or emission portion and an x-ray receiving or image receiving portion located generally or as practically possible 180 degrees from each other and mounted on a rotor (not shown) relative to a track of image capturing portion 108. Image capturing portion 108 can be operable to rotate 360 degrees during image acquisition. Image capturing portion 108 may rotate around a central point or axis, allowing image data of the patient to be acquired from multiple directions or in multiple planes. Surgical navigation system 100 can include those disclosed in U.S. Pat. Nos. 8,842,893, 7,188,998; 7,108,421; 7,106; 825; 7,001,045; and 6; 940,941; the entire contents of each of these references being incorporated by reference herein.

In some embodiments, surgical navigation system 100 can include C-arm fluoroscopic imaging systems, which can generate three-dimensional views of a patient. The position of image capturing portion 108 can be precisely known relative to any other portion of imaging device 104. In some embodiments, a precise knowledge of the position of image capturing portion 108 can be used in conjunction with a tracking system 110 to determine the position of image capturing portion 108 and the image data relative to the patient.

Tracking system 110 can include various portions that are associated or included with surgical navigation system 100. In some embodiments, tracking system 110 can also include a plurality of types of tracking systems, such as, for example, an optical tracking system that includes an optical localizer, such as, for example, sensor array 112 and/or an EM tracking system that can include an EM localizer. Various tracking devices can be tracked with tracking system 110 and the information can be used by surgical navigation system 100 to allow for a display of a position of an item, such as, for example, a patient tracking device 114, an imaging device tracking device 116, and an instrument tracking device, such as, for example, navigation component 30, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to computer 118 where they may be forwarded to surgical navigation computer 120. Image transfer may be performed over a standard video connection or a digital link including wired and wireless. Computer 120 provides the ability to display, via monitor 122, as well as save, digitally manipulate, or print a hard copy of the received images. In some embodiments, images may also be displayed to the surgeon through a heads-up display.

In some embodiments, surgical navigation system 100 provides for real-time tracking of surgical instrument 12. Sensor array 112 is located in such a manner to provide a clear line of sight with emitter array 50, as described herein. In some embodiments, emitter array 50 communicates with sensor array 112 via infrared technology. Sensor array 112 is coupled to computer 120, which may be programmed with software modules that analyze signals transmitted by sensor array 112 to determine the position of each object in a detector space, as shown in FIG. 1. A processor sends the information to monitor 122, which provides a visual representation of the position of surgical instrument 12 relative to the patient's anatomy to allow the medical practitioner to move surgical instrument 12 to a desired location within the patient's anatomy.

In some embodiments, patient tracking device 114 provides a reference frame. The reference frame may be securely attached to the anatomy in the region of the body which is to receive the implant. By sensing attached patient tracking device 114, computer 120 can determine the position of the anatomy in the detector space. Sensor array 112 receives and triangulates signals generated by emitter array 50 to identify the relative position of each of the reference points and surgical instrument 12. The processor and computer 120 modify the image data set according to the identified relative position of each of the reference points during the procedure. The position and trajectory of surgical instrument 12 provided by emitter array 50 is processed by the processor and the computer, and is visually displayed against the preoperative image data set stored in the computer to provide the medical practitioner with a visual representation of the position, path and/or trajectory of surgical instrument 12 relative to a portion of the patient's anatomy and the depth of surgical instrument 12 within the patient's anatomy.

Figure 6:
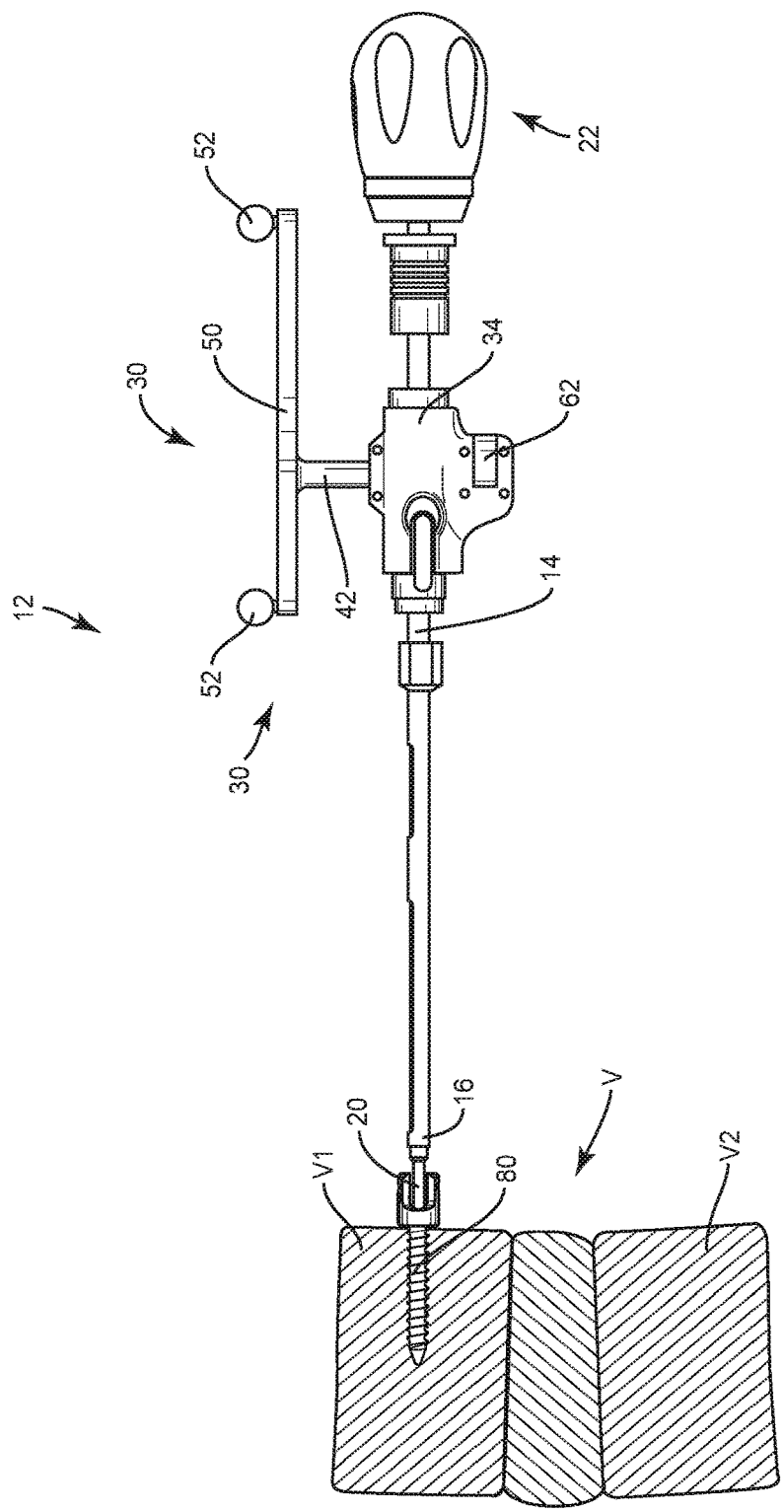
FIG. 6 is a side view of components of one embodiment of a surgical system in accordance with the principles of the present disclosure disposed with vertebrae.

In assembly, operation and use, surgical system 10, similar to the systems and methods described herein, is employed with a surgical procedure for treatment of a spinal disorder affecting a section of a spine of a patient, as discussed herein. For example, the components of surgical system 10 can be used with a surgical procedure for treatment of a condition or injury of an affected section of the spine including vertebrae V, as shown in FIGS. 1 and 6. In some embodiments, one or more of the components of surgical system 10 can be delivered or implanted as a pre-assembled device or can be assembled in situ. In some embodiments, one or more of the components of surgical system 10 may be completely or partially revised, removed or replaced.

The components of surgical system 10 can be employed with a surgical treatment of an applicable condition or injury of an affected section of a spinal column and adjacent areas within a body, such as, for example, vertebrae V. In some embodiments, the components of surgical system 10 may be employed with one or a plurality of vertebra, such as, for example, vertebrae V1 and vertebra V2. To treat a selected section of vertebrae V, a medical practitioner obtains access to a surgical site including vertebrae V in any appropriate manner, such as through incision and retraction of tissues. In some embodiments, the components of surgical system 10 can be used with any existing surgical method or technique including open surgery, mini-open surgery, minimally invasive surgery and percutaneous surgical implantation, whereby vertebrae V are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of components of surgical system 10 including surgical instrument 12 that comprises, such as, for example, a driver adjacent an area within the patient's body, such as, for example, vertebra V1. In some embodiments, a dilator (not shown) is delivered through the surgical passageway adjacent a surgical site within the patient's body to space tissue.

Navigation component 30 is assembled with surgical instrument 12 such that housing 32 is attached with shaft 14, as described herein. Implant engaging surface 20 of end 16 comprises a hexalobe drive surface that engages a corresponding socket surface of a spinal implant, such as, for example, a bone screw 80.

Surgical instrument 12 is positioned such that surface 20 is connected with bone screw 80 for mating engagement therebetween. Surgical instrument 12 is oriented such that emitter array 50 is disposed in a selected orientation, which includes a selected alignment and communication with sensor array 112 to display imaging from monitor 122, as described herein. Gyroscope 60 is powered such that wheel 62 rotates about axis X2, in a clockwise or a counter-clockwise direction, as described herein.

A medical practitioner manipulates, translates and/or rotates surgical instrument 12 into engagement with bone screw 80, as described herein. The medical practitioner manipulates and/or powers surgical instrument 12, such as, for example, by rotating surface 20 in a clockwise direction to drive, torque, insert or otherwise connect bone screw 80 with vertebra V1.

In some embodiments, as the medical practitioner manipulates and/or powers surgical instrument 12 to connect bone screw 80 with vertebra V1, emitter array 50 can be urged out of the selected orientation. Gyroscope 60 conserves angular momentum, as described herein, such that variation in the selected orientation of emitter array 50 is resisted and/or prevented with an equal and opposite force as generated by wheel 62. Gyroscope 60 reacts to change in the orientation of emitter array 50 such that the net force effect is zero to resist and/or prevent movement of navigation component 30 and/or emitter array 50 from the selected orientation. In some embodiments, as surgical instrument 12 is manipulated, emitter array 50 can be urged and/or moved from the selected orientation by tilting, translation and/or rotation of surgical instrument 12. In some embodiments, movement out of the selected orientation causes an interruption of communication between sensor array 112 and surgical instrument 12 and an interruption of the display of imaging from monitor 122, which can cause tissue damage and hazard to the patient.

Sensor array 112 receives signals from emitter array 50 and imaging of surgical instrument 12 and/or bone screw 80 is displayed from monitor 122 via surgical navigation system 100. In some embodiments, maintaining emitter array 50 in communication with sensor array 112 provides display and visualization of positioning of surgical instrument 12 and/or bone screw 80 relative to the patient anatomy during a surgical procedure, as described herein.

In some embodiments, surgical system 10 may comprise various surgical instruments 12 including navigation component 30 of the present disclosure, such as, for example, wires, dilators, taps, awls, inserters, extenders, reducers, spreaders, distracters, blades, retractors, clamps, forceps, elevators and drills, which may be alternately sized and dimensioned, and arranged as a kit.

In some embodiments, the components of surgical system 10 can be made of radiolucent materials such as polymers. Radiomarkers may be included for identification under x-ray, fluoroscopy, CT or other imaging techniques. Upon completion of the surgical procedure, the surgical instruments, assemblies and non-implant components of surgical system 10 are removed from the surgical site and the incision is closed.

Figure 7:
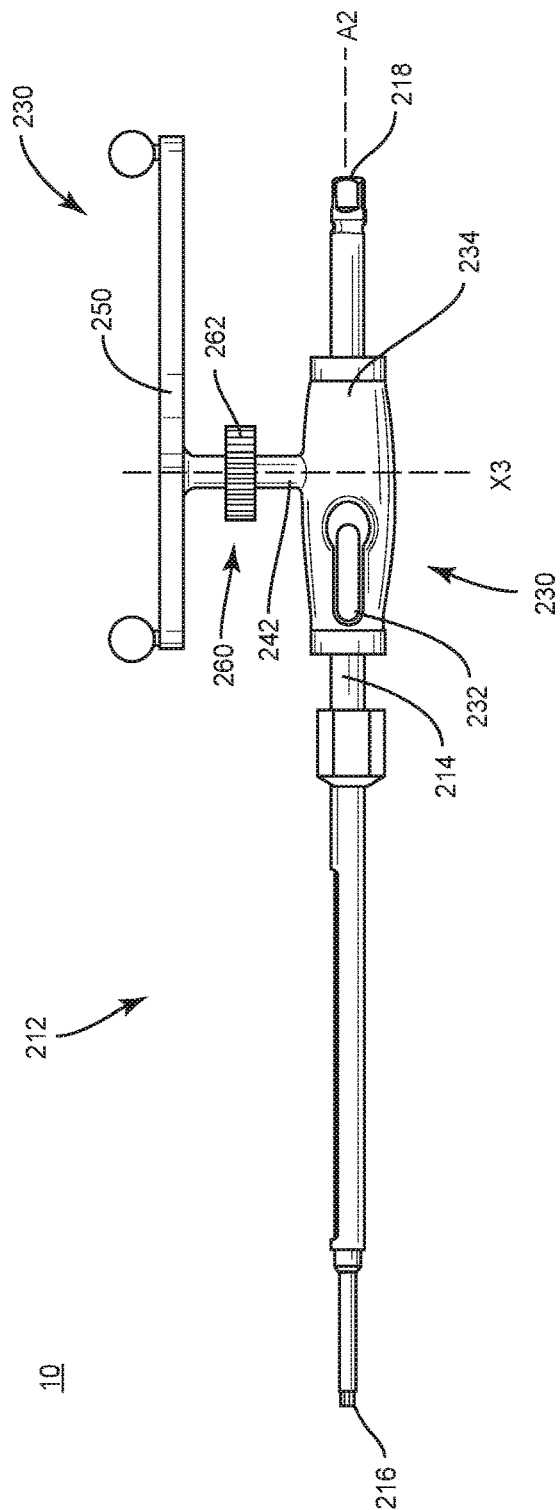
FIG. 7 is a perspective view of components of one embodiment of a surgical system in accordance with the principles of the present disclosure.
Figure 8:
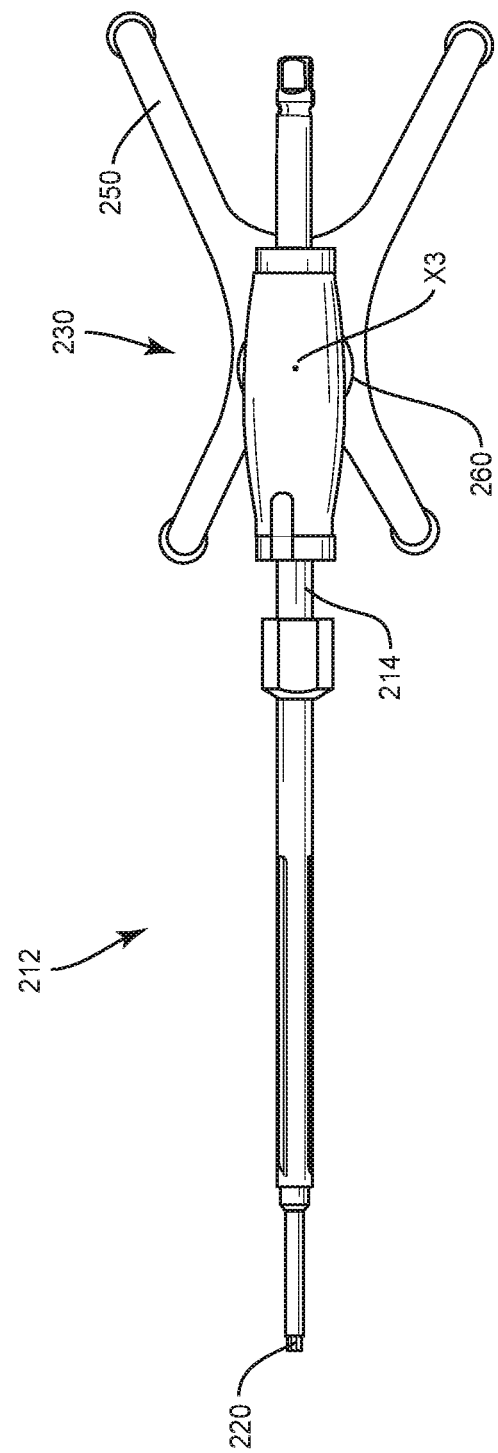
FIG. 8 is a side view of components shown in FIG. 7.

In one embodiment, as shown in FIGS. 7 and 8, surgical system 10, similar to the systems and methods described above with regard to FIGS. 1-6, comprises a surgical instrument 212, similar to surgical instrument 12 described herein. Surgical instrument 212 includes a shaft 214 that extends between an end 216 and an end 218, similar to ends 16, 18 described herein. Shaft 214 defines a longitudinal axis A2. End 216 includes an implant engaging surface 220, similar to surface 20 described herein.

Shaft 214 is configured for connection with an image guide, such as, for example, a navigation component 230, similar to navigation component 30 described herein. Surgical instrument 212 is configured for disposal adjacent a surgical site such that navigation component 230 is oriented relative to sensor array 112 of surgical navigation system 100 of surgical system 10, as shown in FIG. 1 and described herein.

Navigation component 230 includes a housing 232, similar to housing 32 described herein, configured for disposal with shaft 214. Housing 232 is rotatable relative to shaft 214 about axis A2. Housing 232 includes a collar 234, similar to collar 34 described herein. Housing 232 includes a post 242 extending from collar 234. Post 242 defines an axis X3. Post 242 extends perpendicular to axis A2 and is rotatable with housing 232 relative to shaft 214 about axis A2. Navigation component 230 includes a tracking device having an emitter array 250, similar to emitter array 50 described herein, which extends from and is connected to housing 232 via post 242.

Housing 232 includes a stabilizer, such as, for example, a gyroscope 260, similar to gyroscope 60 described herein, mounted for rotation about post 242. Gyroscope 260 is positioned between emitter array 250 and shaft 214/housing 232. As such, emitter array 250 and gyroscope 260 are disposed laterally to shaft 214 and housing 232. In some embodiments, housing 232 may define a cavity for disposal of gyroscope 260.

Gyroscope 260 includes a spinning wheel 262, similar to wheel 62 described herein, which is manipulated and/or powered, as described herein, to rotate relative to housing 232. Wheel 262 rotates about axis X3 such that gyroscope 260 maintains an alignment and/or orientation of navigation emitter array 250 relative to sensor array 112 to communicate a signal representative of a position of surgical instrument 212 and/or an implant connected thereto, as housing 232 is urged and/or moved to rotate and/or translate about and/or relative to axis A2 of shaft 214 during manipulation of surgical instrument 212 in a surgical procedure, similar to that described herein. Wheel 262 is configured to rotate about axis X3 to maintain the alignment and/or orientation of emitter array 250 for communicating the signal relative to sensor array 112. Rotation of wheel 262 is configured to resist and/or prevent movement of navigation component 230 from the alignment and/or orientation for communicating the signal representative of the position of surgical instrument 212 relative to sensor array 112.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a housing;
a member extending through opposite ends of the housing;
an image guide comprising a post having a first end that is fixed to the housing, the post defining an axis, the image guide comprising an emitter array that is fixed to an opposite second end of the post, the emitter array comprising markers for identification under an imaging technique, the emitter array being oriented relative to a sensor to communicate a signal representative of a position of the member to a sensor array; and
a stabilizer disposed within a cavity of the housing such that the stabilizer is rotatable about the axis, the stabilizer being configured to resist and/or prevent movement of the emitter array from the orientation.

2. A surgical instrument as recited in claim 1, wherein the stabilizer generates an angular momentum to resist and/or prevent movement of the emitter array from the orientation.

3. A surgical instrument as recited in claim 1, wherein the stabilizer includes a gyroscope.

4. A surgical instrument as recited in claim 1, wherein the gyroscope includes a spinning wheel.

5. A surgical instrument as recited in claim 3, wherein the stabilizer defines a spin axis disposed co-axial with the axis defined by the post.

6. A surgical instrument as recited in claim 1, wherein the stabilizer includes a counter-balance weight.

7. A surgical instrument as recited in claim 1, wherein the stabilizer includes an electrical power source.

8. A surgical instrument as recited in claim 1, wherein the stabilizer includes a battery.

9. A surgical instrument as recited in claim 1, wherein the stabilizer includes a pneumatic power source.

10. A surgical instrument as recited in claim 1, wherein the stabilizer includes a compressed air cartridge.

11. A surgical instrument as recited in claim 1, further comprising the sensor, wherein the sensor communicates with a processor to generate data for display of an image on a monitor, the image representing position of the member relative to a body.

12. A surgical instrument as recited in claim 1, further comprising the sensor, wherein a camera includes the sensor.

13. A surgical instrument as recited in claim 1, wherein the member includes a tap, a drill or a screwdriver.

14. A surgical instrument comprising:
a collar;
a driver extending through opposite ends of the collar;
an image guide comprising a post having a first end that is fixed to the collar, the post defining an axis, the image guide comprising an emitter array that is fixed to an opposite second end of the post, the emitter array comprising markers for identification under an imaging technique, the emitter array being oriented relative to a sensor to communicate a signal representative of a position of the driver to a sensor array; and
a gyroscope disposed within a cavity of the collar, the gyroscope having a spin axis aligned with the axis, the gyroscope being configured to resist and/or prevent movement of the emitter array from the orientation.

15. A surgical instrument as recited in claim 14, wherein the gyroscope includes a spinning wheel that defines the spin axis.

16. A surgical instrument as recited in claim 14, wherein the sensor communicates with a processor to generate data for display of an image on a monitor.

17. A surgical system comprising:
a tracking device including a housing; and
a surgical instrument comprising a handle and a shaft that extends through opposite ends of the housing, the shaft including opposite first and second ends, the first end comprising a mating surface that engages a mating surface of the handle to couple the handle to the shaft, the second end comprising an implant engaging surface comprising a square, triangular, hexagonal, polygonal, star, torx or hexalobe cross section configured to engage a correspondingly shaped portion of a spinal implant,
the tracking device comprising a post having a first end that is fixed to the housing, the post defining an axis, the tracking device comprising an emitter ray that is fixed to an opposite second end of the post, the emitter ray being oriented relative to a sensor to communicate a signal representative of a position of the surgical instrument to a sensor array, the tracking device including a stabilizer disposed within a cavity of the housing such that the stabilizer is rotatable about the axis and configured to resist and/or prevent movement of the emitter ray from the orientation, the tracking device including a sensor that receives the signal and communicates with a processor to generate data for display of an image on a monitor, the image representing position of the surgical instrument relative to a body.

18. A surgical instrument as recited in claim 1, wherein the housing is rotatable relative to the member about an axis defined by the member.

19. A surgical instrument as recited in claim 1, wherein the member is positioned between the emitter array and the stabilizer.

20. A surgical instrument as recited in claim 1, wherein an inner surface of the housing defines the cavity, the stabilizer comprising a spinning wheel positioned in the cavity that extends through an opposite outer surface of the housing.

* * * * *

UNITED STATES PATENT AND TRADEMARK OFFICE
CERTIFICATE OF CORRECTION

PATENT NO. : 10,285,715 B2
APPLICATION NO. : 14/977161
DATED : May 14, 2019
INVENTOR(S) : Peters et al.

It is certified that error appears in the above-identified patent and that said Letters Patent is hereby corrected as shown below:

In the Specification

Column 5, Line 58, delete "configured engage" and insert -- configured to engage --, therefor.

Column 9, Lines 38-39, delete "7,106;825; 7,001,045; and 6; 940,941;" and insert -- 7,106,825; 7,001,045; and 6,940,941;" --, therefor.

Column 12, Line 11, delete "distracters," and insert -- distractors, --, therefor.

In the Claims

Column 14, Line 37, Claim 17, delete "emitter ray" and insert -- emitter array --, therefor.

Column 14, Line 38, Claim 17, delete "emitter ray" and insert -- emitter array --, therefor.

Column 14, Lines 44-45, Claim 17, delete "emitter ray" and insert -- emitter array --, therefor.

Signed and Sealed this
Twenty-seventh Day of August, 2019

Andrei Iancu
*Director of the United States Patent and Trademark Office*